United States Patent [19]

Lo

[11] Patent Number: 4,560,510
[45] Date of Patent: Dec. 24, 1985

[54] PROCESS AND INTERMEDIATES FOR THE PREPARATION OF ARYL SUBSTITUTED PYRIDO[1,4]BENZODIAZEPINES

[75] Inventor: Young S. Lo, Richmond, Va.

[73] Assignee: A. H. Robins Company, Incorporated, Richmond, Va.

[21] Appl. No.: 597,413

[22] Filed: Apr. 6, 1984

[51] Int. Cl.[4] ............................................ C07D 471/04
[52] U.S. Cl. ................................................ 260/244.4
[58] Field of Search ..................................... 260/244.4

[56]  References Cited
U.S. PATENT DOCUMENTS 4,447,361  5/1984  Taylor .............................. 260/244.4
4,480,100  10/1984  Lo .................................... 260/244.4

Primary Examiner—Paul R. Michl

[57] ABSTRACT

A process for preparing pyrido[1,4]benzodiazepines having antidepressant activity illustrated by the formula:

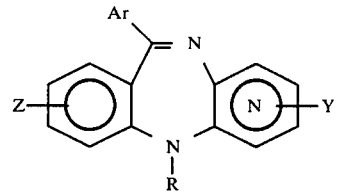

wherein Ar is pyridinyl, thienyl or phenyl; R is alkali-metal ion, hydrogen, loweralkyl or an amine or an amine precursor on the end of a hydrocarbon chain and wherein in the process condensation of an amino-chloropyridine with an aryl(aminophenyl)methanone is accomplished with a strong non-nucleophilic base in stirrable admixture with an inert liquid carrier. Alternatively, condensation is accomplished sequentially using titanium tetrachloride first followed by non-nucleophilic base.

13 Claims, No Drawings

PROCESS AND INTERMEDIATES FOR THE PREPARATION OF ARYL SUBSTITUTED PYRIDO[1,4]BENZODIAZEPINES

BACKGROUND OF THE INVENTION

1. Field of Invention

The present invention relates to a process for the preparation of certain known pyrido[1,4]benzodiazepines and novel chemical intermediates therefor.

An important aspect of the process is the utilization of a strong non-nucleophilic base such as sodium hydride to bring about condensation of an aminochloropyridine and an aryl(aminophenyl)methanone in admixture with mobile inert liquid carrier to produce the pyrido[1,4-]benzodiazepines. Alternatively, the condensation may be started with titanium tetrachloride and finished with the non-nucleophilic base, in which case novel intermediates are produced and used.

2. Information Disclosure Statement

The aryl substituted pyrido[1,4]benzodiazepines prepared by the process of this invention are disclosed in S. African Pat. No. 81/7866 hereby incorporated by reference and are the subject of a corresponding commonly assigned U.S. continuation application Ser. No. 395,218 filed July 6, 1982, now U.S. Pat. No. 4,447,361, hereby incorporated by reference. In the method of preparation disclosed in these references, amino-halo pyridines and aminoarylphenones are heated neat to give pyrido[1,4-]benzodiazepines.

Commonly assigned U.S. application Ser. No. 431,997 filed Sept. 30, 1982, now U.S. Pat. No. 4,480,100, describes preparation of [2-[(nitropyridinyl)amino]phenyl]arylmethanones, useful in preparation of the pyrido[1,4]benzodiazepines, by heating neat a halonitropyridine with an aminoarylphenone.

Heating and reaction of such mixtures as described in the foregoing disclosures involves difficult handling of viscous, sticky reactants and reaction products which adhere to the reaction vessel. In contrast, in the present invention the diazepine ring is formed by a strong non-nucleophilic base such as sodium hydride in a solvent or liquid carrier which provides high mobility, ease of operation and increased yields and direct formation of the sodium salts of the pyrido 1,4-benzoidazepines.

Relating to the preparation of certain chemical intermediates used in the process of the present invention, Yamamoto, M. and Yamamoto H. in Chem. Pharm. Bull. 29(8), 2135-2156 (1981) describe the reaction of 2-amino-4-chlorobenzophenone and an amine in the presence of titanium tetrachloride as represented by the following equation:

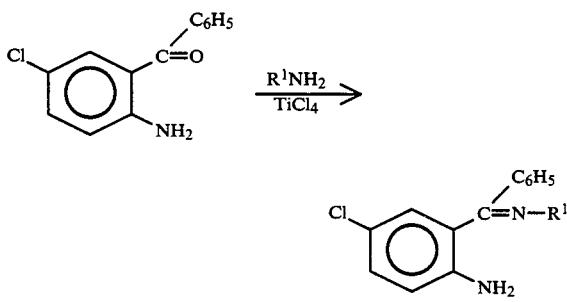

wherein $R^1$=alkyl, cycloalkyl, phenylalkyl, dialkylaminoalkyl and 4-morpholinoalkyl.

Also relating to preparation of certain other intermediates used in the process is a disclosure of phase-transfer catalyzed N-monoalkylation of 2-aminobenzophenones of Mouzin, G., et al, in Synthesis Communications Georg. Thieme Verlag 1981, p. 448–449. as represented by the following equation:

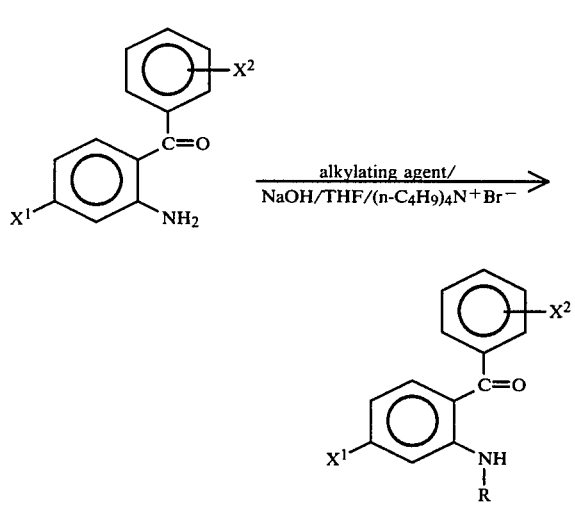

wherein R=$CH_3$, —$C_2H_5$ or allyl; $X^1$=Cl or Br; $X^2$=H, Cl or F.

SUMMARY OF THE INVENTION

Pyridobenzodiazepine compounds which are prepared directly by the novel process of the present invention have the formula:

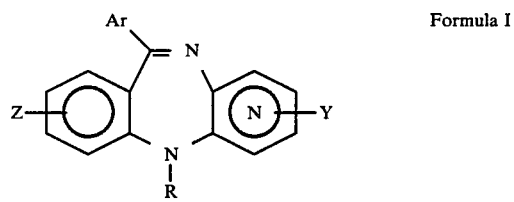

Formula I wherein R is selected from the group consisting of alkali-metal cation ($M^+$), hydrogen, —$alk^1$—Q wherein Q is selected from hydrogen, halo, —$NR^1R^2$, —N=CH—O—$C_2H_5$ or

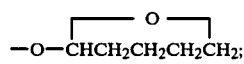

—O—$CHCH_2CH_2CH_2CH_2$;

$R^1$ and $R^2$ are selected from the group consisting of loweralkyl, —C(O)O—loweralkyl or $R^1$ and $R^2$ taken together with the adjacent nitrogen atom may form a heterocyclic residue selected from the group consisting of 1-piperidinyl, 1-phthalimido, 1-pyrrolidinyl, 4-morpholinyl, 1-piperazinyl, and 4-substituted-piperazin-1-yl;

Ar is selected from the group consisting of 2, 3 and 4-pyridinyl, 2 or 3-thienyl, phenyl or phenyl substituted by 1 to 3 radicals selected from halo, loweralkyl, loweralkoxy, trifluoromethyl or nitro and may be the same or different;

alk¹ is a straight or branched hydrocarbon chain containing 1-8 carbon atoms;

Z is selected from the group consisting of hydrogen, halogen, loweralkyl, loweralkoxy, hydroxy or nitro;

Y is selected from the group consisting of hydrogen or 1-2 radicals selected from loweralkyl, loweralkoxy or hydroxy and may be the same or different, and the acid addition salts thereof except when R=M⁺.

The compounds of Formula I have utility as antidepressant pharmaceuticals or as intermediates in the preparation of other compounds of Formula I and of Formula $I_p$ described hereinbelow.

Additionally, the compounds of Formula I wherein R is $$-alk^1-O-\overset{\overset{\displaystyle O}{\displaystyle |\underline{\quad\quad}|}}{CHCH_2CH_2CH_2CH_2}$$

have been used to prepare compounds of Formula I wherein R is —alk¹—R¹R² via novel intermediates wherein R is alk¹—OH and alk¹—OSO₂W wherein W is as defined hereinbelow.

In the further definition of symbols in the formulas hereon and where they appear elsewhere throughout this specification and claims, the terms have the following significance.

The "alk" straight or branched connecting hydrocarbon chain containing 1-8 carbons is exemplified by methylene (—CH₂—), ethylene (—CH₂—CH₂—), propylene (—CH₂CH₂CH₂—), ethylidene [—CH—],
                                                    |
                                                    CH₃

1,2-propylene [—CH—CH₂— or —CH₂—C—],
                |                    |
                CH₃                  CH₃
                                      |
                                      H CH₃
            |
isopropylidine [—C—], or 1,3-butylene [—CH—CH₂—CH₂—],
            |                           |
           CH₃                          CH₃ and the like.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl, and the like.

The term "halogen" includes chlorine, bromine, fluorine, and iodine, preferably chlorine, bromine and fluorine.

The term "4-substituted-1-piperazinyl" refers to piperazine substituted in the 4-position by loweralkyl or alkoxy-carbonyl blocking group which may subsequently be removed to give the unsubstituted piperazine.

Pharmaceutically acceptable acid addition salts are those salts formed by the pyridobenzodiazepines prepared by the process of this invention with any acid which is physiologically compatible in warm blooded animals, such salts being formed either by strong or weak acids. Representative of strong acids are hydrochloric, sulfuric and phosphoric acids. Representative of weak acids are fumaric, maleic, succinic, oxalic, cyclohexamic and the like.

The 6-aryl-11H-pyrido[2,3-b][1,4]benzodiazepines and the 5,6-dihydro derivatives thereof encompassed by Formula I have the formula:

$I_w$

The 6-aryl-11H-pyrido[3,4-b][1,4]benzodiazepines and the 5,6-dihydro derivatives thereof encompassed by Formula I have the formula:

$I_x$

The 10-aryl-5H-pyrido[4,3-b][1,4]benzodiazepines and the 10,11 dihydro derivatives thereof encompassed by Formula I have the formula:

$I_y$

The 10-aryl-5H-pyrido[3,2-b][1,4]benzodiazepines and the 10,11-dihydro derivatives thereof encompassed by Formula I have the formula:

$I_z$

In all the formulas $I_w$ to $I_z$, the symbols R, Ar, Z and Y have the definition given hereinabove under Formula I.

For the purpose of testing antidepressant activity of the present invention compounds, the procedure given by Englehardt, E. L., et al., J. Med. Chem. 11(2): 325 (1968) which has been indicative in the past of usefulness of compounds for treating human depression was used as follows: 20 mg/kg of the compound to be tested was administered to five adult female mice (ICR-DUB strain) intraperitoneally 30 minutes prior to the administration of a ptotic dose (32 mg/kg IP) of tetrabenazine (as the methanesulfonate salt). Thirty minutes later the presence or absence of complete eyelid closure (ptosis)

was assessed in each animal. An ED$_{50}$ (Median Effective Dose) may be established for each tested compound in blocking tetrabenazine-induced ptosis in mice following the procedure given by Litchfield et al., J. Pharmacol. Exp. Therap. 96: 99–113 (1949).

Compounds preparable by the process of the invention or from the intermediates thereof which have antidepressant activity in the foregoing antidepressant test procedure have the Formula $I_p$

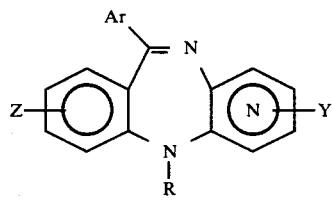

wherein;

R is selected from the group consisting of hydrogen, loweralkyl or —alk$^1$—N—R$^1$R$^2$;

R$^1$ and R$^2$ are selected from the group consisting of hydrogen, loweralkyl or R$^1$ and R$^2$ taken together with the adjacent nitrogen atom may form a heterocyclic residue selected from the group consisting of 1-pyrrolidinyl, 4-morpholinyl, 1-piperazinyl or 4-loweralkyl-1-piperazinyl;

Ar is selected from the group consisting of 2, 3 or 4-pyridinyl, 2 or 3-thienyl, phenyl or phenyl substituted by 1 to 3 radicals selected from halo, loweralkyl, loweralkoxy, trifluoromethyl or nitro and may be the same or different;

Alk$^1$ is a straight or branched hydrocarbon chain containing 1–8 carbon atoms;

Z is selected from the group consisting of hydrogen, halogen, loweralkyl, loweralkoxy, hydroxy or nitro;

Y is selected from the group consisting of hydrogen, or 1–2 radicals selected from loweralkyl, loweralkoxy or hydroxy and may be the same or different, and the pharmaceutically acceptable acid addition salts.

The compounds of Formula $I_p$ wherein R is —alk$^1$—NR$^1$R$^2$ and R$^1$ and R$^2$ are loweralkyl or hydrogen have been shown to have low incidence of antihistaminic, anti-cholinergic and cardiotoxic side effects when tested in animals.

The preferred pyridobenzodiazepines useful in the method of treating depression are as follows:

Compound active ingredient (free base)

N,N-dimethyl-6-phenyl-11H-pyrido[2,3-b][1,4]benzodiazepine-11-propanamine.
6-(4-fluorophenyl)-N,N-dimethyl-11H-pyrido[2,3-b][(1,4]benzodiazepine-11-propanamine.
6-phenyl-1H-pyrido[2,3-b][1,4]benzodiazepine-11-propanamine.
N-methyl-6-phenyl-11H-pyrido[2,3-b][1,4]benzodiazepine-11-propanamine.
6-(2-chlorophenyl)-N,N-dimethyl-11H-pyrido[2,3-b][1,4]benzodiazepine-11-propanamine.
6-(2-fluorophenyl)-N,N-dimethyl-11H-pyrido[2,3-b][1,4]benzodiazepine-11-propanamine.

The generalized schematic equation for the preparation of pyridobenzodiazepines according to the process of the invention is given in Chart I.

CHART I

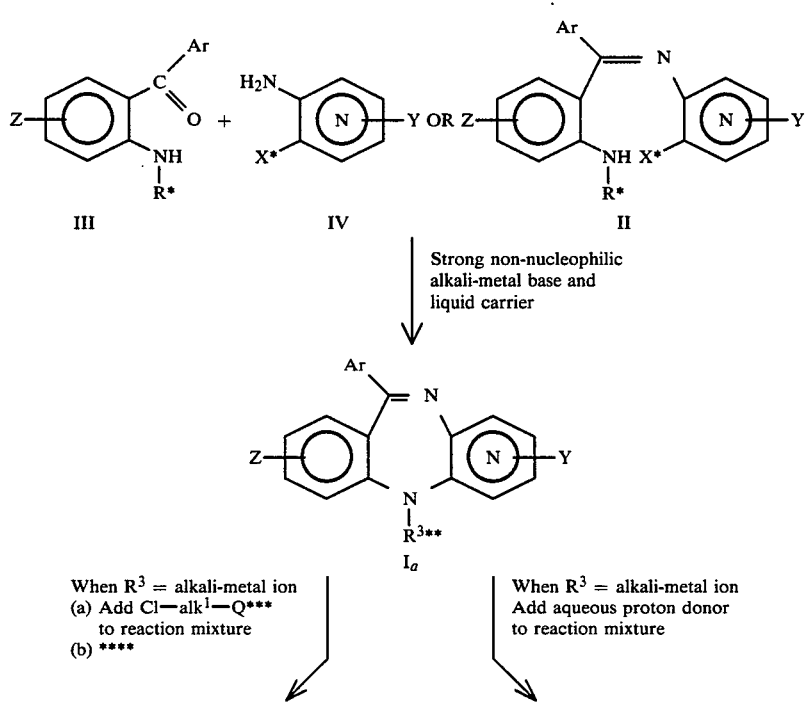

CHART I

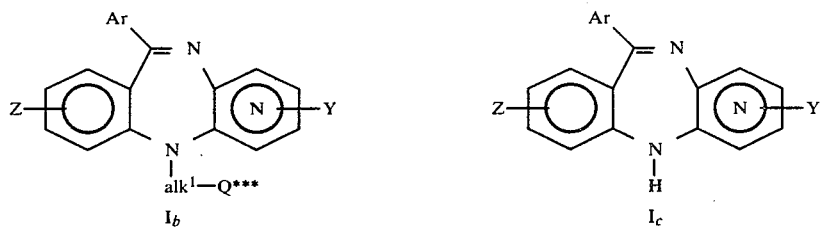

*R = hydrogen, loweralkyl, —alk¹—NR¹R², —alk¹—N=CH—OC₂H₅ or

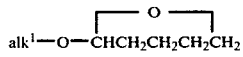

and R¹ and R² are as defined under Formula I. X = chlorine, bromine, fluorine or iodine.

**R³ = alkali-metal ion, loweralkyl, —alk¹—NR¹R², —alk¹—N=CH—OC₂H₅ or

and R¹ and R² are as defined in Formula I.

***Q = hydrogen, halo, —alk¹—N=CH—OC₂H₅, alk¹—NR¹R² or

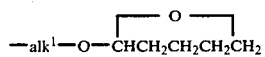

and R¹ and R² are as defined under Formula I.

****Add dimethylformamide to the reaction mixture when Q is

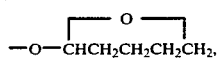

hydrogen, halo and —alk¹N=CH—OC₂H₅.

Compounds of Formulas $I_a$, $I_b$ and $I_c$ are encompassed by Formula I.

Additional procedures for converting compounds of Formulas Ia or Ib wherein Q is

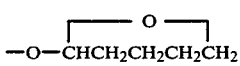

which have been separated from the reaction mixture (or which have been prepared by reacting isolated compounds wherein R³ is H with sodium hydride and reagent

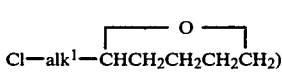

to useful antidepressant agents (Formula VIII) are illustrated in the schematic equation of Chart II.

CHART II

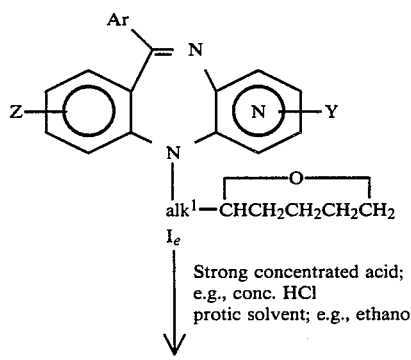

Strong concentrated acid;
e.g., conc. HCl
protic solvent; e.g., ethanol

-continued
CHART II

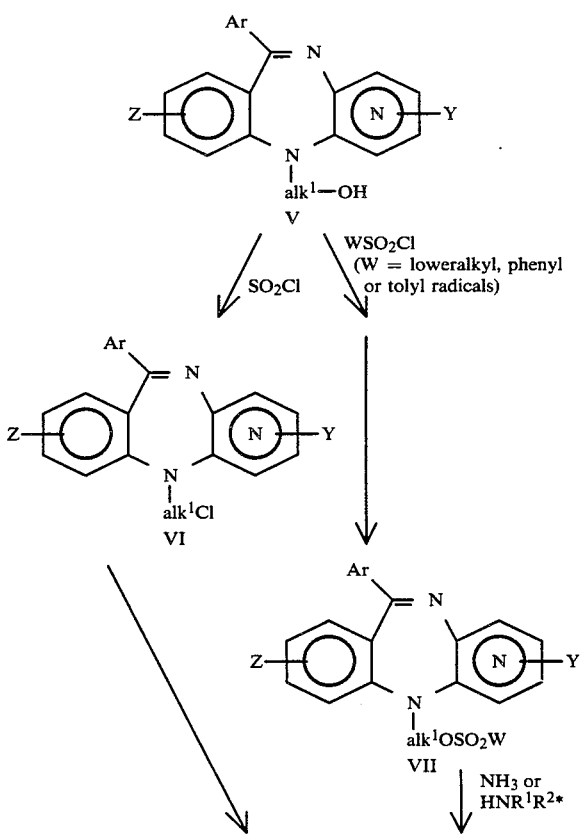

-continued
CHART II

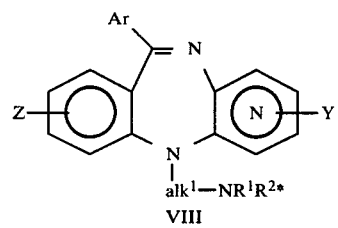
VIII

*R¹ and R² are as defined in Formula I + hydrogen.

Compounds of Formula $I_e$ and VI are encompassed by Formula I and Formula VIII is encompassed by $I_p$.

Compounds of Formula $I_e$, V and VII are novel.

Novel intermediates useful in the preparation of pyridobenzodiazepines of Formula I have the formula:

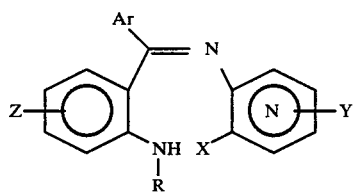

Formula II wherein Ar, Y and Z are the same as defined under Formula I; X=halo (Cl, Br, F, I) and R is selected from the group consisting of hydrogen, loweralkyl, —alk-¹—NR¹R², —alk¹—N=CH—OC₂H₅ or

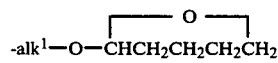

wherein alk¹, R¹ and R² are the same as defined under Formula I and the acid addition salts thereof.

All positions of the pyridinyl nitrogen encompassed by Formula II are illustrated as follows:

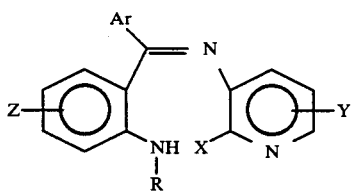
$II_a$

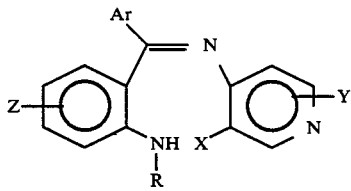
$II_b$

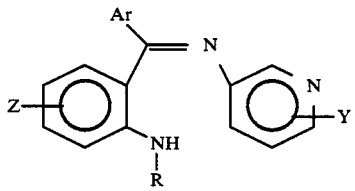
$II_c$

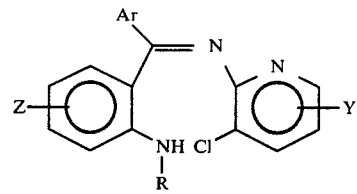
$II_d$

Compounds of Formula II are novelly prepared according to the following generalized schematic equation:

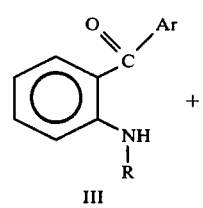
III

+

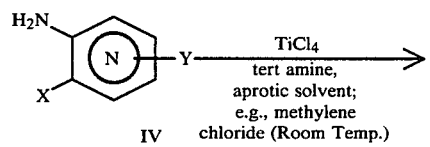
IV

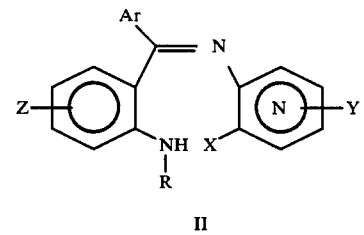
II

X=halo,
R=H or —alk¹—Q, wherein Q=H or —NR¹R².
Compounds of Formula II are novel.
Compounds of Formula IV are available commercially or can be readily prepared by known methods.
Compounds of Formula III wherein R is H and corresponding to the Formula IIIa

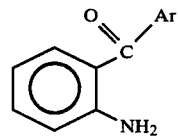
$III_a$ are available commercially or may be prepared by known methods.

Novel compounds of Formula III wherein R is —alk-¹—Q and Q is H or —NR¹R² are prepared according to the following generalized schematic equation from compounds of Formula IIIa

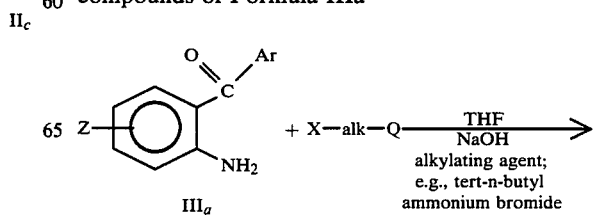

-continued

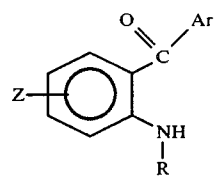

IIIb wherein X is halo, R is selected from —alk¹NR¹R², alk¹—N=CH—OC₂H₅ or

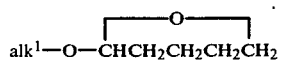

and Ar, Z and R¹R² are as defined under Formula I, and the acid addition salts thereof.

It is therefore an object of the present invention to provide a novel process for the preparation of aryl-11H-pyrido[1,4]benzodiazepines which are either antidepressant pharmaceutical agents or useful in the preparation of other aryl-11H-pyrido[1,4]benzodiazepine agents which have antidepressant activity which utilizes a strong nucleophilic base in the condensation of (aminophenyl)arylmethanones and an amino-chloropyridine or partially condensed intermediates from those reactants all in stirrable admixture with inert liquid carrier.

Another object is to provide novel chemical intermediates and process therefor, such intermediates being useful in the preparation of arylpyridobenzodiazepines, which intermediates in general terms are phenylamines linked adjacent to the amine function via phenyl-substituted iminomethylene bridge to halopyridine and process therefor.

Still another object is to provide certain novel (aminophenyl)arylmethanones useful as intermediates in the process of the invention.

DETAILED DESCRIPTION OF THE INVENTION

The novel process of the invention for preparing compounds of Formula I is comprised of the following four steps 1 to 4 with an optional preliminary step A.

Step 1, reacting a compound of the formula

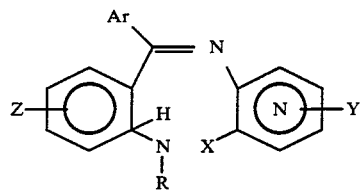

II or a mixture of compounds of the formulas

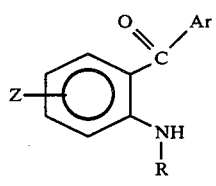  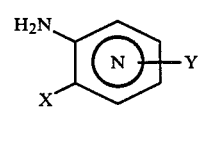

III    IV wherein Ar, Y and Z are as defined under Formula I, X is halo (chlorine, bromine, fluorine or iodine), R is hydrogen or alk¹—Q wherein alk¹ is as defined above and Q is selected from hydrogen, —NR¹R², —N=CH—OC₂H₅, or

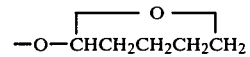

and R¹ and R² are selected from loweralkyl, —C(O)O—loweralkyl or R¹ and R² taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl together with at least a stoichiometric amount of a strong non-nucleophilic alkali-metal base in stirrable admixture with inert liquid carrier to give a compound of the formula

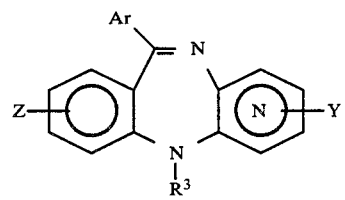

in stirrable admixture with inert liquid carrier, wherein Ar, Y and Z are as defined above and R³ is an alkali-metal ion selected from sodium, potassium or lithium or —alk¹—Q, wherein alk¹ is as defined above and Q is the same as in the starting compound.

Step 2, optionally when desired, reacting a compound as prepared in step 1 in admixture with said liquid carrier wherein R³ is an alkali-metal ion with a proton source to give a compound of the formula

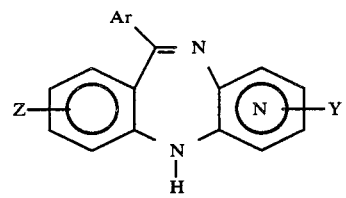

in admixture with inert liquid carrier wherein Ar, Z and Y are as defined above.

Step 3, when desired, reacting a compound as prepared in admixture with liquid carrier in step 1 wherein R³ is an alkali-metal ion with a reagent having the formula

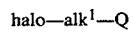

halo—alk¹—Q wherein Q is selected from hydrogen, —NR¹R², —N=CH—O—C₂H₅, or

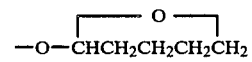

and R¹ and R² are selected from the group consisting of loweralkyl, —C(O)O—loweralkyl or R¹ and R² taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl, to give a compound of the formula

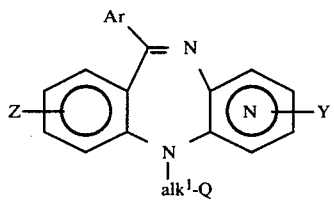

in admixture with liquid carrier wherein Q has the starting value of the reagent and Ar, Y, Z and —alk$^1$ are as defined above.

Step 4, separating a compound prepared in step 1 other than a compound wherein R$^3$ is an alkali-metal cation, and in steps 2 and 3 by conventional means from the carrier and the reaction mixture to give a compound of the formula

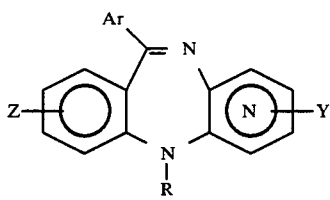

wherein Ar, Y, Z and R are as defined above, except R is not alkali-metal cation, and the acid addition salts thereof.

In another novel variation of the process in a preliminary Step A, compounds of Formula II, when used in step 1, see Chart 1, are prepared as follows:

Step A, reacting a mixture of a compound of the formula

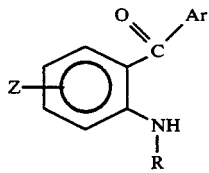

wherein Ar, Z and R are as defined in step 1 of the formula

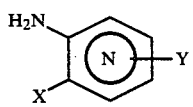

wherein X is halogen and Y is as defined under Formula I, together with titanium tetrachloride and an excess of a tertiary organic amine in an inert liquid carrier and separating the product from the reaction mixture.

Obviously, Step A also serves as a single process step for preparing compounds of Formula II, see Chart I, which, as stated above, are novel chemical intermediates.

The following description is applicable to the foregoing process:

In step 1, suitable liquid carriers must be non-reactive with the strong non-nucleophilic base; e.g., sodium hydride and other reactants free of moisture and stable enough to prevent development of alkaline metal hydroxides which lead to impurities which are difficult to remove. Carriers generally classified as strictly protic are not suitable. Suitable liquid carriers may or may not solubilize the reactants or products but some solubility of organic reactants and products in the carrier is usually desirable. Examples of aprotic aromatic non-polar solvents which are suitable as carriers are toluene, xylene and benzene. Examples of aprotic non-polar ether solvents which are suitable carriers are tetrahydrofuran, dioxane, and ethyleneglycol dimethyl ether. Examples of aprotic polar solvents which are suitable as carriers are dimethylformamide, morpholinoformamide, alkyl-2-pyrrolidinones, pyridine and dimethylsulfoxide. A preferred carrier is toluene. Use of mixtures of these carriers have been demonstrated to have advantage and such advantage will depend on the specific reactants or products involved, particularly when solubility is a factor. One such preferred mixture involves toluene and tetrahydrofuran. Another preferred combination is toluene and dimethylformamide as in the case when the radical

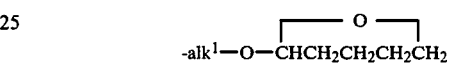

is involved. The amount of carrier may vary widely ranging from as little as about 5 parts per 100 parts by weight of reactants to as much as 100 parts or more per 100 parts by weight of reactants. Generally, the minimum amount of carrier which can be used is that amount of carrier which will provide sufficient mobility for the reaction mixture to become stirrable and to provide flowability to the mix. When toluene is used, about 8–12 parts by weight of carrier to reaction mixture is a preferred range. A wide range of temperatures in step 1 may be employed, suitably about 20° C. to 150° C., about 40° C. to 120° C. being preferred. The more specific preferred temperature is that obtained with boiling tetrahydrofuran and refluxing toluene; i.e 65° C. to 110° C. While it is possible to conduct the reaction using a stoichiometric amount of sodium hydride, more complete reaction is obtained by using at least one molar excess of base. Two molar equivalents of strong alkali-metal non-nucleophilic base; e.g., sodium hydride, is therefore preferred. One preferred mode of conducting the reaction in step 1 is to slurry or dissolve the aminohalopyridine in a suitable aprotic carrier, preferably toluene, and simultaneously add a slurry of the non-nucleophilic alkali-metal base in the same carrier and a solution of the aminobenzophenone in a suitable aprotic non-polar solvent, preferably tetrahydrofuran or dioxane, at a temperature such that the tetrahydrofuran boils off during the addition as the aminobenzophenone is reacted. As indicated above, sodium, potassium or lithium hydrides are suitable strong non-nucleophilic bases which facilitate the reaction, making possible the use of the solvent carriers and are preferred, sodium hydride being especially preferred. Among other strong, non-nucleophilic bases which may be used are potassium tertiary butoxide, sodium triphenylmethane, sodium dimethylsulfoxide, and alkali-metal amides.

The following illustrates the balanced equation involved in step 1 for each type of reactants when the strong non-nucleophilic alkali-metal base is sodium hydride.

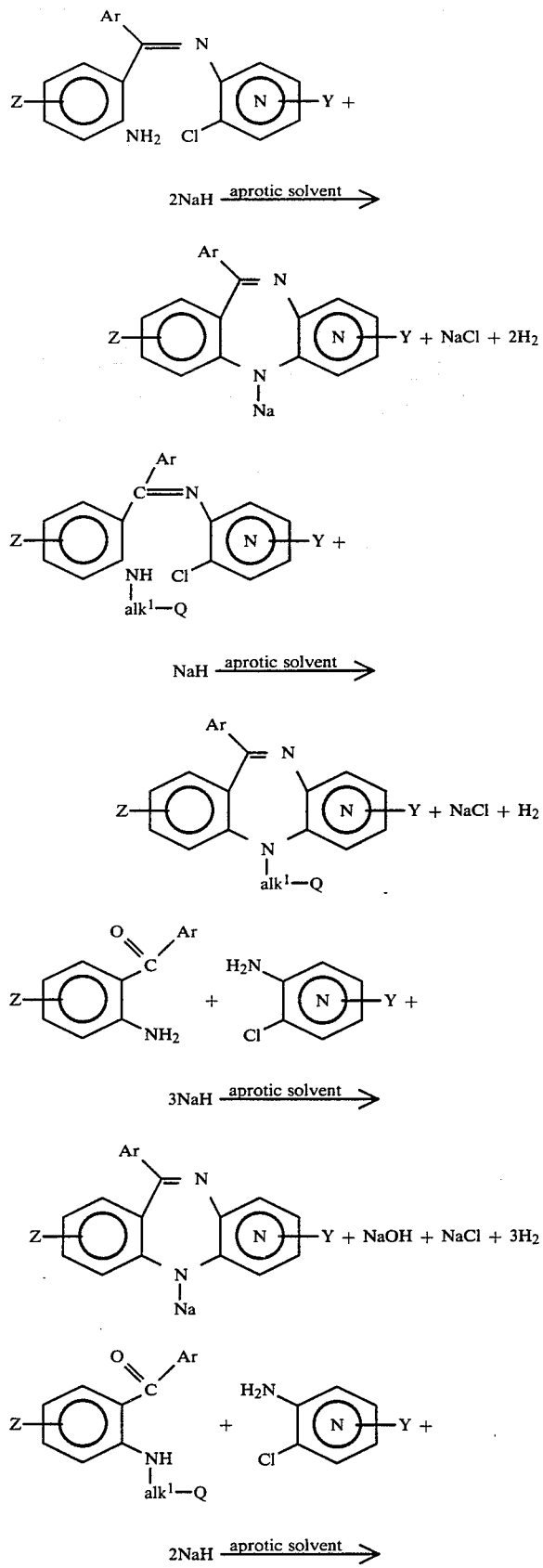

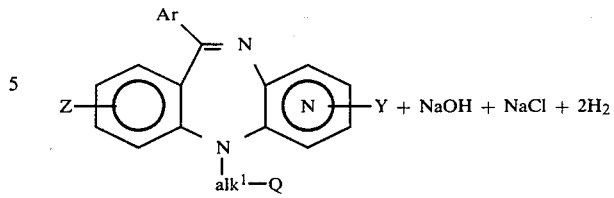

In each instance it is preferable to use an excess of sodium hydride.

In step 2, an alkali-metal salt of compounds as prepared in step 1 still in the liquid carrier are converted to the

compounds by reacting with any reagent capable of providing a proton source. Examples of suitable agents are water, weak or strong acids, and water containing buffering salts. The latter agent is preferred and the preferred buffering salt is ammonium chloride. Blueish green color of the solution present initially in this step is indicative of the sodium salt of the pyridobenzodiazepine and as the proton source is added such as aqueous ammonium chloride solution, a golden yellow solid precipitates.

In step 3, the halo—alk¹—Q reagent in a suitable organic solvent is added to the reaction mixture containing a metal salt; i.e., $R^3$=alkali-metal ion, and the reaction mixture is heated until reaction is complete. Solvents used to dissolve the reagent are generally the same as used for the carrier in step 1, except when Q is pyranoyloxy=

halo or —N=CH—OC₂H₅, dimethylformamide is used. The reaction mixture is filtered to remove halo salt by-product.

In step 4, the products may be isolated, (a) by extraction, preferably by partitioning between water and methylene chloride; (b) by chromatographic separation; (c) by conversion to acid addition salts and recrystallizing from suitable solvent or solvent combinations; (d) by dissolving the strong acid salts such as the hydrochloride in water and extracting out impurities with a solvent such as toluene.

In preliminary step A, compounds of Formula II are substantially separated from liquid carrier by conventional means such as evaporating solvents and partitioning between water and organic solvent, filtering to remove titanium oxide, washing, drying and evaporating the solvent layer to give the product as residue which can be used directly in step 1. The product may be further purified by chromatography or recrystallization from organic solvents.

A preferred procedure for conducting the combination of steps 1 and 3 (i.e., when step 2 is not involved) is to simultaneously add a tetrahydrofuran or dioxane solution of a compound of the formula

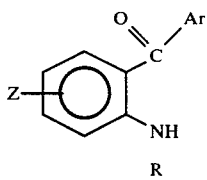

wherein Ar, R and Z are as defined in step 1 and a slurry of sodium hydride in toluene to a hot toluene solution of a pyridine compound of the formula

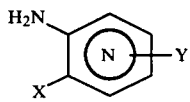

wherein X and Y are as defined in step 1 at a rate such that the tetrahydrofuran or dioxane is distilled away at about the same rate it is being added and thereafter adding a toluene solution containing a reagent having the formula halo—alk$^1$—Q wherein alk$^1$ and Q are as defined in step 3, except in the in the instance where Q is

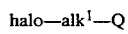

halo or —N=CH—OC$_2$H$_5$ in which case the solvent for the halo—alk$^1$—Q reagent preferred is dimethylformamide.

A preferred embodiment is the use in step 1 of a mixture of compounds of said formulas

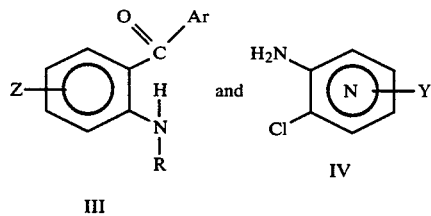

Another preferred embodiment is the use in step 1 of a mixture of compounds of formulas III and IV and a strong base consisting of sodium hydride.

A further preferred embodiment is the use in step 1 of a mixture of compounds of formulas III and IV wherein R is H.

A still further preferred embodiment is the use in step 1 of a mixture of compounds of formulas III and IV wherein R is H and the strong base is sodium hydride.

Another preferred embodiment is the use in step 1 of a mixture of compounds of formulas III and IV consisting of 2-aminobenzophenone and 3-amino-2-chloropyridine and a strong base consisting of sodium hydride in step 1 to produce the sodium salt of 6-phenyl-11H-pyrido[2,3-b][1,4]benzodiazepine in step 2.

As an extension of the process outlined in steps 1–4 above with or without optional step A, the following further optional steps (see Chart II) are novelly employed to obtain certain compounds of Formulas I and I$_p$ in steps 5 to 8. As will be recognized, the generic scope of compounds preparable is extended to include R=OH, —alk$^1$—OSO$_2$—alkyl, alk$^1$—OSO$_2$—phenyl and one or both of R$^1$ and R$^2$ are H.

Step 5, reacting a novel compound obtained in step 4 of the formula

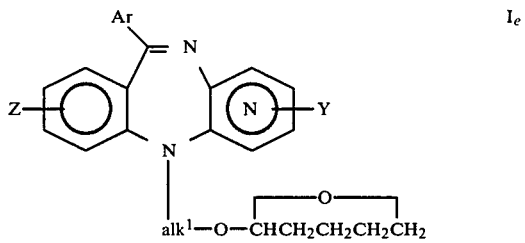

wherein Ar, Y, Z and alk$^1$ are as defined under Formula I with a strong concentrated acid in protic solvent, preferably ethanol, to give a novel compound of the formula

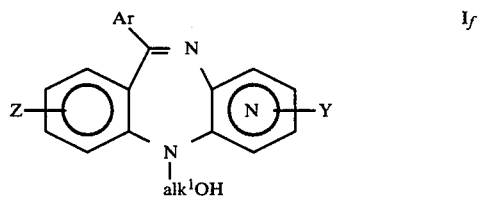

wherein Ar, Y, Z and alk$^1$ are as defined above.

Step 6, reacting a compound prepared in step 5 with thionyl chloride to obtain a compound of the formula

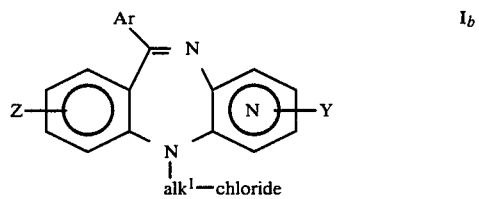

wherein Ar, Y, Z and alk$^1$ are as defined above.

Step 7, reacting a compound prepared in step 5 with a reagent

WSO$_2$Cl wherein W is loweralkyl, phenyl or tolyl to give a compound of the formula

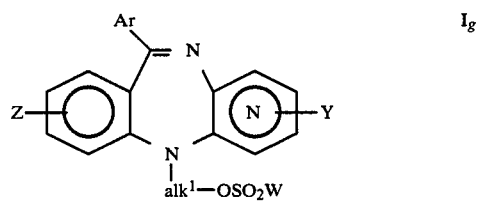

wherein Ar, Y, Z, alk$^1$ and W are as defined above.

Step 8, reacting a compound prepared in steps 6 or 7 with a secondary or primary amine of the formula

HNR$^1$R$^2$ wherein R[1] and R[2] are selected from hydrogen, loweralkyl, and —NR[1]R[2] may be a heterocyclic radical as defined under Formula I, to give a compound of the formula

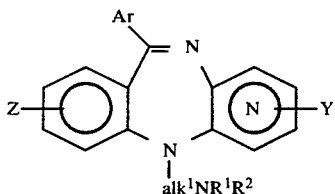

wherein Ar, Y, Z, alk[1] and R[1], R[2] and —NR[1]R[2] are as defined above.

Primary amines may be prepared by reacting compounds wherein —NR[1]R[2] is phthalimido with hydrazine hydrate and acid

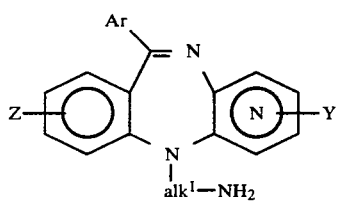

Compounds prepared by the process wherein Q is —NHC(O)O-loweralkyl may be reacted with lithium aluminum hydride to prepare secondary amines of the formula

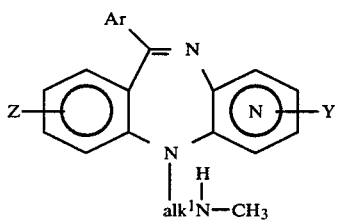

Compounds wherein Q is —N=CH—OC$_2$H$_5$ may also be reacted with sodium borohydride to prepare secondary amines.

The following preparations 1 and 2 illustrate the method for preparing aryl-(2-amino-substituted-phenyl)methanone of Formula III wherein R is other than hydrogen (see Chart II) and are not to be construed as being limiting in nature.

Preparation 1

[2-[[3-(Dimethylamino)propyl]amino]phenyl]phenyl-methanone monohydrochloride

To a mixture of 78.8 g (0.4 mole) of 2-aminobenzophenone, 160 g (4.0 mole) of crushed sodium hydroxide and 8 g of tetra-n-butyl ammonium bromide was added a dry solution of 145.8 g (1.2 mole) of 3-dimethylaminpropyl chloride in 700 ml of tetrahydrofuran. The mixture was stirred mechanically and was maintained at reflux overnight. The tetrahydrofuran solution was decanted and concentrated. The concentrate was dissolved in toluene. The solid from which the tetrahydrofuran was decanted was dissolved in water and extracted with the toluene solution. The resulting toluene layer was separated and washed twice with water and then extracted three times with portions of 20% acetic acid totaling 600 ml. The combined acetic acid solution was washed once with toluene and then made basic with 50% sodium hydroxide in the presence of toluene. The aqueous layer was separated and extracted once with toluene. The toluene layers were combined and washed with water, dried over sodium sulfate and evaporated to give 112.8 g (100%) of nearly pure free base of the title compound. A 20 g sample was dissolved in 75 ml of isopropyl alcohol to which was added 0.076 mole of hydrogen chloride dissolved in about 35 ml isopropyl alcohol. Additional isopropyl alcohol and isopropyl ether (about 1:1 ratio) were added to make a total volume of about 200 ml. The mixture was stirred overnight. The yellow solid was collected by filtration, washed once with 1:1 isopropyl alcohol/isopropyl ether and twice with isopropyl ether. Weight of product obtained from the 20 g sample was 16.4 g, m.p. 182°–183° C.

Analysis:

Calculated for C$_{18}$H$_{23}$N$_2$OCl: C,67.81; H, 7.27; N,8.79

Found: C,67.68; H,7.29; N,8.70

Preparation 2

Following the procedure of Preparation 1 but substituting the following for 3-dimethylaminopropyl chloride, 3-(1-pyrrolidinyl)propylamine,
3-(1-piperidinyl)propylamine, and
3-(4-morpholinyl)propylamine,
there are obtained:

[2-[[3-(1-pyrrolidinyl)propyl]amino]phenyl]phenylmethanone,

[2-[[3-(1-piperidinyl)propyl]amino]phenyl]phenylmethanone, and

[2-[[3-(4-morpholinyl)propyl]amino]phenyl]phenylmethanone.

The following examples are provided merely by way of illustration and are not to be construed as being limiting in nature.

EXAMPLE 1

N-[(2-Aminophenyl)phenylmethylene]-2-chloro-3-pyridinamine

To a stirred suspension of 3.94 g (0.02 mole) of 2-aminobenzophenone and 2.58 g (0.02 mole) of 3-amino-2-chloropyridine in 20 ml of toluene and 6.2 ml (0.048 mole) of triethylamine under a nitrogen blanket in an ice bath was added a solution of 2.28 g (0.012 mole) of titanium tetrachloride in 10 ml of toluene over a 5 min period. After the addition was complete, the ice bath was removed. The mixture became dark red in color and solid material was in evidence. About 15 ml of toluene was added followed by 15 ml of methylene chloride. After 1 hr total time, TLC showed starting material and product were present. After 3 hr total time, additional titanium chloride, 1.52 g (0.08 mole), in 4.15 ml (0.032 mole) of triethylamine and methylene chloride was added to the reaction mixture which was then stirred overnight. The mixture was evaporated. The residue was partitioned between water and methylene chloride. Solid precipitate was removed by filtration. The aqueous layer was separated and extracted again with methylene chloride. The methylene chloride layers were combined and back washed with sodium chloride solution, dried over sodium sulfate and evaporated to give 6.2 g of orange oil. The chemical ionization mass spectrometer gave product peak at m/e 308 and starting materials peaks at m/e 198 and m/e 129. NMR analysis as follows indicated the product was composed of about 75% of the title compound. The $^1$HNMR spectrum of the crude subject product was obtained in CDCl$_2$ containing 1% tetramethylsilane (TMS). The chemical shifts, multiplicities and assignments are given below.

Mixture of compounds A, B, and C (structures shown).

| Chemical Shifts (multiplicities) at ppm | Assignments |
| --- | --- |
| 7.50 (multiplet) | Ha in Compound A |
| 7.35 (multiplet) | Hb in Compound B |
| 7.30–5.95 (multiplet) | signals from other protons attached to carbons on Compounds A, B and C |
| 5.40 (broad singlet) | —NH signals |
| 4.83 (singlet) | CH$_2$Cl$_2$ (methylene chloride) |

Ratio of the integrations at 7.50 ppm to that at 7.35 ppm is roughly 3:1, thus the product is about 75% A.

EXAMPLE 2

N-[(2-Aminophenyl)phenylmethylene]-2-chloro-3-pyridinamine

To a stirred suspension of 7.88 g (0.04 mole) of 2-aminobenzophenone and 5.14 g (0.04 mole) of 3-amino-2-chloropyridine in 100 ml of methylene chloride and 27.2 ml (0.2 mole) of triethylamine under nitrogen blanket was added a solution of 5.28 ml of titanium tetrachloride in 20 ml of methylene chloride dropwise over a 10 min period. The reaction mixture was stirred at room temperature for 22 hr. Water was added slowly to the reaction mixture until a thick suspension was formed. The suspension was poured into 150 ml of water and the resulting mixture was stirred for 15 min. The mixture was filtered to remove titanium dioxide. The filter cake was rinsed with methylene chloride. The organic layer of the filtrate was separated. The aqueous layer was extracted once with methylene chloride. The methylene chloride layers were combined, washed with dilute sodium bicarbonate solution, dried and evaporated to give 12.6 g of brown syrup. NMR analysis as follows indicated the product was composed mainly of title compound with about 15% 3-amino-2-chloropyridine starting material contaminant. The $^1$HNMR spectrum of the crude subject product was obtained in CDCl$_3$ containing 1% tetramethylsilane (TMS). The chemical shifts, multiplicities and assignments are given below.

Mixture of compounds A, B, and C (structures shown).

| Chemical Shifts (multiplicities) at ppm | Assignments |
| --- | --- |
| 7.70 (multiplet) | Ha in Compound A |
| 7.55 (multiplet) | Hb in Compound B |
| 5.55 (broad singlet) | NH signals |
| 5.00 (singlet) | CH$_2$Cl$_2$ (methylene chloride) |
| 7.40–610 (multiplet) | signals from remainder of protons on Compounds A, B and C. |

Ratio of the integrations at 7.70 ppm to that at 7.55 ppm is roughly 13 to 2; thus the product is about 85% A.

EXAMPLE 3

Following the procedure of Example 2 but substituting the following for 3-amino-2-chloropyridine,
4-amino-3-chloropyridine,
3-amino-4-chloropyridine, and
2-amino-5-chloropyridine
there are obtained:
(a) N-[(2-aminophenyl)phenylmethylene]-3-chloro-4-pyridineamine,
(b) N-[(2-aminophenyl)phenylmethylene]-4-chloro-3-pyridinamine, and
(c) N-[(2-aminophenyl)phenylmethylene]-3-chloro-2-pyridinamine.

EXAMPLE 4

Following the procedure of Example 2 but substituting the following for 2-aminobenzophenone,
2-amino-4-chlorobenzophenone,
2-amino-4-methylbenzophenone,
2-amino-4-methoxybenzophenone,
2-amino-4-hydroxybenzophenone,
2-amino-4-nitrobenzophenone,
2-amino-5-chlorobenzophenone,
2-amino-4'-chlorobenzophenone, and
2-amino-4'-methylbenzophenone,
there are obtained:
(a) N-[(2-amino-4-chlorophenyl)phenylmethylene]-2-chloro-3-pyridinamine,
(b) N-[(2-amino-4-methylphenyl)phenylmethylene]-2-chloro-3-pyridineamine, (c) N-[(2-amino-4-methoxyphenyl)phenylmethylene]-2-chloro-3-pyridinamine,
(d) N-[(2-amino-4-hydroxyphenyl)phenylmethylene]-2-chloro-3-pyridinamine,
(e) N-[(2-amino-4-nitrophenyl)phenylmethylene]-2-chloro-3-pyridinamine,
(f) N-[(2-amino-5-chlorophenyl)phenylmethylene]-2-chloro-pyridinamine,
(g) N-[(2-aminophenyl)-4-chlorophenylmethylene]-2-chloro-3-pyridinamine, and
(h) N-[(2-aminophenyl)-4-methylphenylmethylene]-2-chloro-3-pyridinamine.

EXAMPLE 5

N'-[2-[(2-Chloro-3-pyridinylimino)phenylmethyl]-phenyl]-N,N-dimethyl-1,3-propanediamine To a mixture of 2.82 g (0.01 mole) of [2-[[3-(dimethylamino)propyl]amino]phenyl]phenylmethanone and 1.29 g (0.01 mole) of 3-amino-2-chloropyridine, 6.2 ml (0.048 mole) of triethylamine and 20 ml of methylene chloride stirred in an ice bath under nitrogen atmosphere was added 2.28 g (0.012 mole) of titanium tetrachloride in 10 ml of methylene chloride during a 5 minute period. The mixture was then stirred at room temperature for 2 days during which time mass spec-CI showed little change in relative intensity of M.W. 129 (starting pyridine) and M.W. 393 (title product). Water was added to the reaction mixture and stirring was continued for 1.5 hr. The mixture was filtered to remove solid and the filter cake was rinsed with methylene chloride. Saturated sodium chloride solution was added to facilitate separation of layers. The methylene chloride layer was washed once with more sodium chloride solution. The aqueous layer having a pH of about 6 was basified to about pH 8-9 with potassium carbonate and then extracted twice with methylene chloride. The latter methylene chloride layers were washed with sodium chloride solution. All the methylene chloride extracts were combined, dried and evaporated to give 4.8 g of semi-solid product. TLC of the product showed it contained evey little starting 3-amino-2-chloropyridine. Mass Spec. analysis showed the presence of compounds with molecular weight corresponding to title product (393), 3-amino-2-chloropyridine (129) and triethylamine (102) but no [2-[[3-(dimethylamino)propyl]amino]phenyl]phenylmethanone.
$^1$HNMR spectrum in CDCl$_3$ containing 1% TMS indicated the product was mostly title compound and some triethylamine. No 3-amino-2-chloropyridine was seen. The chemical shifts, multiplicities and assignments are given below.

A mixture of

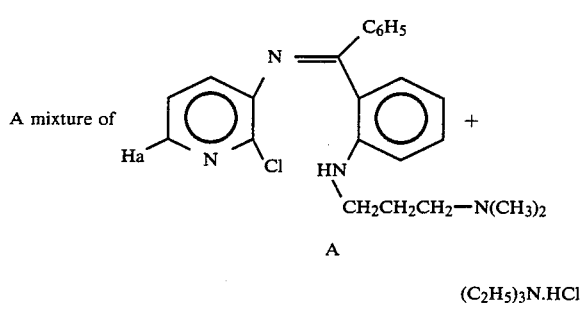

(C$_2$H$_5$)$_3$N.HCl

| Chemical Shifts (multiplicities) at ppm | Assignments |
| --- | --- |
| 9.85–9.40 (multiplet) | NH on A as well as (Et)$_3$N$^+$.H |
| 7.85 (multiplet) | Ha |
| 7.50–6.23 (multiplet) | protons attached to aromatic rings |
| 5.25 (singlet) | CH$_2$Cl$_2$ (methylene chloride) |
| 2.25 (singlet) | N(Me)$_2$ (methyl group signal) |
| 3.70–1.70 (multiplet) | signals from alkylene groups (—CH$_2$—) on compound A as well as triethylamine |
| 1.35 (triplet) | methyl group signals on triethylamine |

EXAMPLE 6

N'-[2-[(2-Chloro-3-pyridinylimino)phenylmethyl]-phenyl]-N,N-dimethyl-1,3-propanediamine To a mixture of 6.37 g (0.02 mole) of [2-[[3-(dimethylamino)propyl]amino]phenyl]phenylmethanone and 2.57 g (0.02 mole) of 3-amino-2-chloropyridine, 16.8 ml (0.12 mole) of triethylamine in 80 ml of methylene chloride stirred in an ice bath under nitrogen atmosphere was added dropwise 2.64 ml (0.024 mole) of titanium tetrachloride in 20 ml of methylene chloride over a 10 min period. The mixture was allowed to cool to room temperature with continued agitation. The following day chemical ionization mass spectrometry showed that the reaction had essentially gone to completion with no starting methanone compound present. TLC showed little of the starting pyridine was present. The mixture was stirred over the weekend. Water was added to the reaction mixture and stirring was continued for 1.5 hr. The mixture was filtered to remove solid and filter cake was rinsed with methylene chloride. Saturated sodium bicarbonate solution was added to facilitate separation of layers. The methylene chloride layer was washed once with more bicarbonate solution. The aqueous layer was washed with methylene chloride and all the methylene chloride extracts were combined, dried and evaporated to give 7.35 g (93.5%) of brown oil. The chemical ionization mass spectrometer gave a signal corresponding to a molecular weight of the title compound at m/e 393.5 and showed a trace of compound at m/e 282 (starting methanone free base) and some compound at m/e 102 (triethylamine) and some compound at m/e 129.5 (starting amino-chloropyridine). The $^1$HNMR spectrum of the subject product was obtained in CDCl$_3$ containing 1% tetramethylsilane (TMS) and is consistent with the proposed structure and with methylene chloride as minor impurity. No signal from starting materials were detected. The chemical shifts, multiplicities and assignments are given below.

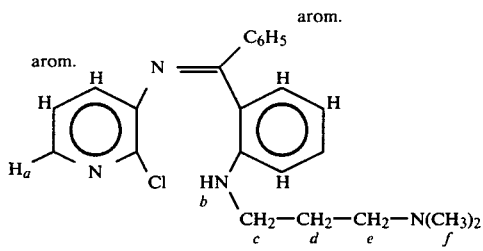

| Chemical Shifts (multiplicities) at ppm | Assignments |
| --- | --- |
| 9.55 (broad singlet) | Hb |
| 7.85 (multiplet) | Ha |
| 7.50 to 6.25 (multiplet) | Haromatic |
| 5.20 (singlet) | CH₂Cl₂ (methylene chloride) |
| 3.50 to 3.15 (quartet) | e |
| 2.15 (singlet) | f |
| 2.55 to 1.70 (multiplet) | c and d |

EXAMPLE 7

6-Phenyl-11H-pyrido[2,3-b][1,4]benzodiazepine-11-pyranoyloxypropyl

To a solution of 10.82 g (0.04 mole) of 6-phenyl-11H-pyrido[2,3-b][1,4]benzodiazepine in 60 ml of dimethylformamide was added 3.2 g (0.08 mole) of sodium hydride as 60% suspension in mineral oil followed by 13.2 ml (0.08 mole) of 1-chloro-3-pyranoyloxypropane. Progress of the reaction was followed via TLC and an additional 0.7 g of 60% sodium hydride was added. After the reaction had stirred for about 3 days, a trace of starting pyridobenzodiazepine remained. The reaction mixture was treated with aqueous ammonium chloride and extracted three times with toluene. The toluene layer was back-washed with water, dried, treated with activated charcoal and filtered. The filtrate was evaporated to give 22.8 g of black oil. The oil was passed through a short column of 45 g silica gel, eluting first with toluene and then toluene-ethyl acetate. Fraction A was concentrated to give 16.3 g of a mixture consisting of 85% title product and 15% 1-chloro-3-pyranoyloxy propane + mineral oil + toluene. Fraction B was concentrated to give 2.4 g residue. Mass spectra of Fraction A showed the following:

m/e 179 which is starting 1-chloro-3-pyranoyloxy propane used in excess, m/e 330 which is a fragment from the product, and m/e 414 which is the title product.

The ¹HNMR spectrum of the subject crude product was obtained and is consistent with the proposed structure and with toluene and 1-chloro-3-pyranoyloxypropane. The chemical shifts, multiplicities and assignments are given below.

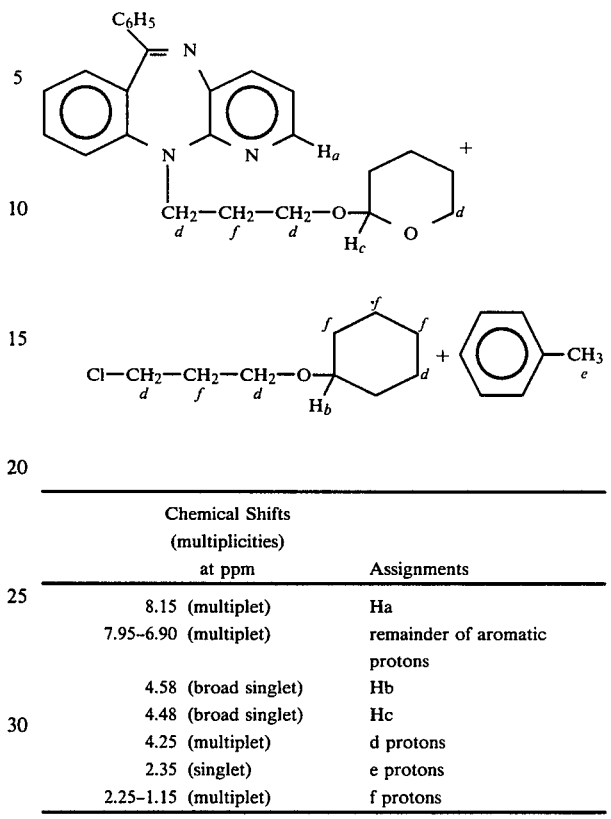

| Chemical Shifts (multiplicities) at ppm | Assignments |
| --- | --- |
| 8.15 (multiplet) | Ha |
| 7.95–6.90 (multiplet) | remainder of aromatic protons |
| 4.58 (broad singlet) | Hb |
| 4.48 (broad singlet) | Hc |
| 4.25 (multiplet) | d protons |
| 2.35 (singlet) | e protons |
| 2.25–1.15 (multiplet) | f protons |

EXAMPLE 8

6-Phenyl-11H-pyrido[2,3-b][1,4]benzodiazepine-11-hydroxypropyl

A mixture of 3.6 g (0.0088 mole) of 6-phenyl-11H-pyrido[2,3-b][1,4]benzodiazepine-11-pyranoyloxypropyl, 3.6 ml of 37% aqueous hydrochloric acid and 15 ml of 190 proof ethanol was stirred overnight. Sodium hydroxide pellets, 1.7 g, was added and the mixture stirred until the pellets had disintegrated. The solvent was evaporated and the residue was partitioned between methylene chloride and water. The aqueous layer was extracted once more with methylene chloride. The combined methylene chloride layers were washed with water, dried and evaporated to give 2.93 g of brown oil which crystallized. The crystals were separated by filtration and washed with isopropyl ether-petroleum ether. On drying, the yellow crystals weighed 1.91 g, m.p. 131°–134° C. Mass spectra of the product showed the following:

m/e 103 which is isopropyl ether which was used as crystallization solvent, m/e 414 which is starting material, trace amount, and m/e 330 which is title product.

The ¹H NMR spectrum of the subject crystalline product was obtained and is consistent with the proposed structure

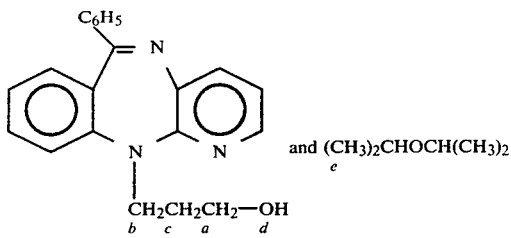 and $(CH_3)_2CHOCH(CH_3)_2$

The chemical shifts, multiplicities and assignments are given below.

| Chemical Shifts (multiplicities) at ppm | Assignments |
| --- | --- |
| 8.20–6.80 (multiplet) | all aromatic protons |
| 4.45–3.50 (multiplet) | a protons |
| 3.65 (where triplet centered) | b protons |
| 2.65 (singlet) | d protons |
| 2.15–1.65 (multiplet) | c protons |
| 1.10 (doublet) | e protons |

EXAMPLE 9

N'-[2-Chloro-6-[(3-chloro-4-pyridinylimino)phenylmethyl]phenyl]-N,N-dimethyl-1,3-propanediamine Following the procedure of Example 6 and substituting [2-[[3-(dimethylamino)propyl]amino]-6-chlorophenyl]phenylmethanone, the title compound is prepared.

EXAMPLE 10

6-Phenyl-11H-pyrido[2,3-b][1,4]benzodiazepine Sodium Salt (Crude Mixture)

To a solution of 516 g (4 mole) of 3-amino-2-chloropyridine in 3.8 liters of toluene were added simultaneously in batches a solution of 830 g (4.2 mole) of 2-aminobenzophenone in 2.2 liters of pyridine and a slurry of 290 g (12 mole) (as 60% in mineral oil) of sodium hydride slurried in 500 ml of toluene over a 2 hr period at reflux. Reflux continued for 3 hr additional. Evolution of hydrogen was vigorous. After stirring overnight at ambient temperature, the mixture was heated to remove a volume of distillate of 3.8 liters which NMR indicated to be 65% toluene and 35% pyridine.

EXAMPLE 11

6-Phenyl-11H-pyrido[2,3-b][1,4]benzodiazepine

To the residual mixture in Example 10 was added cautiously a solution of 440 g (8 mole) of ammonium chloride in 700 ml of water (much foaming). The mixture was heated to remove 1.5 liters of distillate comprised of water, pyridine and toluene. To the residual solution was added 500 ml of toluene and the mixture heated a second time to remove 900 ml of distillate. To the residual solution 500 ml more toluene was added and the mixture was again heated to remove 500 ml of distillate. The orange residual slurry was diluted with 7.2 liters of tetrahydrofuran. The mixture was filtered. The cake was washed by slurrying in 3 liters of hot tetrahydrofuran and the slurry filtered. The filtrates were combined and passed through a silica gel column. The eluent was concentrated and the residue slurried in isopropyl ether-toluene [3:1]. Brown-orange solid was collected by filtration. The filtrate was concentrated and azeotroped with toluene to remove pyridine The residual solution was diluted with isopropyl ether-toluene [1:1] and the solution was refrigerated to obtain yellow crystals. The combined yield of the title compound was 813 g (75%) based on starting materials in Example 10. TLC analysis of the product gave a good comparative result with known title product.

EXAMPLE 12

N,N-Dimethyl-6-phenyl-11H-pyrido[2,3-b][1,4]benzodiazepine-11-propanamine Fumarate [1:1]

A mixture of 920 g (3.4 mole) of 6-phenyl-11H-pyrido[2,3-b][1,4]benzodiazepine prepared in Example 11 (and another small run) in 2 liters of toluene and 1.5 liter of tetrahydrofuran and 84 g (3.5 mole) of sodium hydride (as 60% in mineral oil) was heated at reflux with vigorous evolution of hydrogen. The mixture became black-green in color. To the mixture was added a solution of 7.6 mole of 3-dimethylaminopropyl chloride in 2 liters of toluene and the reaction mixture was heated at reflux for 5 hr and then cooled overnight. The black-yellow mixture was filtered with difficulty mainly to remove sodium chloride. The filtrate was concentrated to remove all but about 1.5–2 liters of toluene. The residual toluene concentrate was diluted with 2 liters of methylene chloride and the solution washed with water. The washed solution was concentrated on a rotary evaporator at 80° C. bath temperature. The remaining black syrup weighed 1400 g. The syrup was poured slowly into a hot solution of 394 g (3.4 mole) of fumaric acid in 4 liters of isopropyl alcohol. The solution was treated with activated charcoal and filtered. The filtrate was seeded and refrigerated overnight. The yellow precipitate was collected by filtration and washed with a small amount of isopropyl ether and dried to give 1491 g (93%) of the fumarate salt. The salt was dissolved in 17.2 liters of isopropyl alcohol and the solution was treated with 75 g of charcoal heated at reflux for 15 min and filtered through a column containing 100 g of Celite which had been wetted with 200 ml of isopropyl alcohol. The filtrate was then stirred for 20 hr. The precipitate was collected by filtration, washing the filter cake with cold isopropyl alcohol followed by 3 liters of isopropyl ether and dried to give 1255 g (85%) of crystalline product. The crystals were triturated with 1 liter of isopropyl ether-methylene chloride (3:1 by vol.) and the mixture subjected to filtration. The cake was vacuum dried at 60° C. overnight under high vacuum, m.p. 174°–175° C., uncorrected.

Analysis:

Calculated for $C_{27}H_{28}N_4O_4$: C,68.63; H,5.97; N,11.86

Found: C,68.48; H,6.00; N,11.80

EXAMPLE 13

N,N-Dimethyl-6-phenyl-11H-pyrido[2,3-b][1,4]benzodiazepine-11-propanemine Fumarate [1:1]

Preparation of Crude Free Base of Title Compound

To a solution of 780 g (6 mole) of 3-amino-2-chloropyridine in 2 liters of toluene at reflux was added simultaneously a solution of 1,320 g (6.6 mole) of 2-aminobenzophenone in 3 liters of tetrahydrofuran and a slurry of 444.0 g (18.5 mole) of sodium hydride in 1.2 liters of toluene over a 3 hr period. (During the addition at reflux, the tetrahydrofuran distilled out at about the same rate it was being added). To the reaction mixture was added 12 moles of 3-dimethylaminopropyl chloride in 3.5 liters of toluene. The mixture was heated at reflux for 5 hr then was allowed to cool, standing overnight at ambient temperature. TLC indicated some 6-phenyl-11H-pyrido[2,3-b][1,4]benzodiazepine was present; therefore, 12 g more sodium hydride was added and the mixture was heated at reflux to complete the reaction. The mixture was allowed to cool somewhat and 2 liters of saturated ammonium chloride and 3 liters of water were added. The aqueous layer was discarded and the toluene layer was washed four times with 2 liters of water each time. The toluene layer was concentrated on a rotary evaporator and finally subjected to high vacuum distillation to remove unreacted 3-dimethylaminopropyl chloride. Yield of crude syrup containing primarily the free base of the title compound was 2,680 g.

Conversion to Fumarate Salt and Purification Thereof

The crude syrup was mixed with 6 moles of fumaric acid in 10 liters of isopropyl alcohol. The precipitate was collected and washed with 3 liters of isopropyl alcohol and recrystallized twice to give 2,200 g of yellow crystals. A sample triturated with a mixture of hot isopropyl ether-methylene chloride [3:1 by volume] gave the following analysis:

Analysis:
Calculated for $C_{27}H_{28}N_4O_4$: C,68.63; H,5.97; N,11.86
Found C,68.23; H,5.99; N,11.87

EXAMPLE 14

N,N-Dimethyl-6-phenyl-11H-pyrido[2,3-b][1,4]benzodiazepine-11-propanamine Fumarate [1:1]

Preparation of Crude Free Base of Title Compound

To a solution of 129 g (1 mole) of 3-amino-2-chloropyridine in 350 ml of toluene at reflux was added simultaneously a solution of 217 g (1.1 mole) of 2-aminobenzophenone in 500 ml of tetrahydrofuran and a slurry of 74.5 g (3.1 mole) of sodium hydride in 250 ml of toluene over a 1.5 hr period. (During the addition at reflux the tetrahydrofuran distilled out at about the same rate it was being added). To the reaction mixture was added 2 moles of 3-dimethylaminopropyl chloride in 600 ml of toluene. The mixture was heated at reflux for 5 hr.

To the black slurry comprised of free base of the title compound and some unreacted sodium hydride and 3-dimethylaminopropyl chloride in toluene (shown by TLC to be free of any 6-phenyl-11H-pyrido[2,3-b][1,4]benzodiazepine) was added 1 mole of ammonium chloride in 800 ml of water. The organic layer was separated and washed with four 500 ml portions of water. The organic layer was concentrated on a rotoevaporator to remove solvent and under high vacuum to remove unreacted 3-dimethylaminopropyl chloride. Yield of dark brown-yellow syrup comprised principally of free base of the title compound was 433 g.

Conversion to Fumarate Salt

The syrup was dissolved in 800 ml of isopropyl alcohol and to the solution was added 1 mole of fumaric acid in 1.5 liters of isopropyl alcohol. The salt crystallized by seeding and separated by filtration.

EXAMPLE 15

6-(2-Thienyl)-11H-pyrido[2,3-b][1,4]benzodiazepine

Following the procedures of Examples 10 and 11 but substituting 2-aminophenyl-(2-thienyl)methanone in Example 10 for 2-aminobenzophenone, the title compound is obtained.

EXAMPLE 16

6-(3-Thienyl)-11H-pyrido[2,3-b][1,4]benzodiazepine

Following the procedures of Examples 10 and 11 but substituting 2-aminophenyl-(3-thienyl)methanone in Example 10 for 2-aminobenzophenone, the title compound is obtained.

EXAMPLE 17

6-(2-Pyridinyl)-11H-pyrido[2,3-b][1,4]benzodiazepine

Following the procedures of Examples 10 and 11 but substituting 2-aminophenyl-(2-pyridinyl)methanone for 2-aminobenzophenone in Example 10, the title compound is obtained.

EXAMPLE 18

6-(3-Pyridinyl)-11H-pyrido[2,3-b][1,4]benzodiazepine

Following the procedures of Examples 10 and 11 but substituting 2-aminophenyl-(3-pyridinyl)methanone for 2-aminobenzophenone in Example 10, the title compound is obtained.

EXAMPLE 19

6-(4-Pyridinyl)-11H-pyrido[2,3-b][1,4]benzodiazepine

Following the procedures of Examples 10 and 11 but substituting 2-aminophenyl-(-pyridinyl)methanone for 2-aminobenzophenone in Example 10, the title compound is obtained.

EXAMPLE 20

Following the procedure of Example 12 but substituting the following for 6-phenyl-11H-pyrido[2,3-b][1,4]benzodiazepine:
6-(2-thienyl)-1H-pyrido[2,3-b][1,4]benzodiazepine,
6-(3-thienyl)-11H-pyrido[2,3-b][1,4]benzodiazepine,
6-(2-pyridinyl)-11H-pyrido[2,3-b][1,4]benzodiazepine,
6-(3-pyridinyl)-11H-pyrido[2,3-b][1,4]benzodiazepine,
and, 6-(4-pyridinyl)-11H-pyrido[2,3-b][1,4]benzodiazepine,
there are obtained:
(a) N,N-dimethyl-6-(2-thienyl)-11H-pyrido[2,3-b][1,4]benzodiazepine-11-propanamine fumarate,
(b) N,N-dimethyl-6-(3-thienyl)-11H-pyrido[2,3-b][1,4]benzodiazepine-11-propanamine fumarate,
(c) N,N-dimethyl-6-(2-pyridinyl)-11H-pyrido[2,3-b][1,4]benzodiazepine-11-propanamine fumarate,
(d) N,N-dimethyl-6-(3-pyridinyl)-11H-pyrido[2,3-b][1,4]benzodiazepine-11-propanamine fumarate, and
(e) N,N-dimethyl-6-(4-pyridinyl)-11H-pyrido[2,3-b][1,4]benzodiazepine-11-propanamine fumarate.

EXAMPLE 21

Following the procedure of Example 5 but substituting the following for [2-[[3-(dimethylamino)propyl]amino]phenyl]phenylmethanone:
[2-[[3-(1-pyrrolidinyl)propyl]amino]phenyl]phenylmethanone,
[2-[[3-(1-piperidinyl)propyl]amino]phenyl]phenylmethanone, and
[2-[[3-(4-morpholinyl)propyl]amino]phenyl]phenylmethanone,
there are obtained:
N-[2-[(2-chloro-3-pyridinylimino)-3-(1-pyrrolidinyl)-propanamine, N-[2-[(2-chloro-3-pyridinylimino)-3-(1-piperidinyl)-propanamine, and N-[2-[(2-chloro-3-pyridinylamino]-3-(4-morpholinyl)-propanamine,

EXAMPLE 22

N,N-Dimethyl-6-phenyl-11H-pyrido[2,3-b][1,4]benzodiazepine-11-propanamine Fumarate [1:1]

To a solution of 2.5 g (0.00637 mole) of N'-[2-[(2-chloro-3-pyridinylimino)phenylmethyl]phenyl]-N,N-dimethyl-1,3-propanediamine obtained in Example 5 in 20 ml of toluene (solution was dried by azeotroping using a Dean Stark trap and cooled) was added 0.62 g (0.0128 mole) of sodium hydride as 50% mineral oil suspension added to a small amount of toluene. The mixture was heated at reflux for 3 hr. Water was added cautiously. The toluene layer was washed twice with water and extracted twice with 1N aqueous hydrochloric acid solution. The aqueous acidic layer was washed with toluene. The aqueous layer was then basified with 50% sodium hydroxide solution in the presence of toluene. The aqueous layer was extracted twice with toluene. The toluene layers were combined, charcoaled, filtered and evaporated to give 2.03 g of brown oil, the free base of the title compound (89.5% yield). The oil was dissolved in isopropyl alcohol and 0.7 g fumaric acid was added with warming. The solution was seeded with known title compound and allowed to stand about 15 hr at room temperature. Isopropyl ether was added with stirring for 15 min. The solid was collected by filtration and washed once with isopropyl alcohol-isopropyl ether mix and once with isopropyl ether. On air drying, 2.4 g (80%), m.p. 168°-170° C. was obtained. The melting point, NMR analysis and Mass Spec. analysis were comparable to known title compound.

EXAMPLE 23

Following the procedure of Example 22 but substituting the following for N'-[2-[(2-chloro-3-pyridinylimino)phenylmethyl]phenyl]-N,N-dimethyl-1,3-propanediamine:

N-[2-[(2-chloro-3-pyridinylimino)-3-(1-pyrrolidinyl)-propanamine,

N-[2-[(2-chloro-3-pyridinylimino)-3-(1-piperidinyl)-propanamine, and

N-[2-[(2-chloro-3-pyridinylimino)-3-(4-morpholinyl)-propanamine, there are obtained:

6-phenyl-11-[3-(1-pyrrolidinyl)propyl]-11H-pyrido[2,3-b][1,4]benzodiazepine fumarate, 6-phenyl-11-[3-(1-piperidinyl)propyl]-11H-pyrido[2,3-b][1,4]benzodiazepine fumarate, and 6-phenyl-11-[3-(4-morpholinyl)propyl]-11H-pyrido[2,3-b][1,4]benzodiazepine fumarate, using ethanol-ethyl acetate recrystallizing solvent in the latter.

What is claimed is:

1. A process for the preparation of a pyridobenzodiazepine compound having the formula:

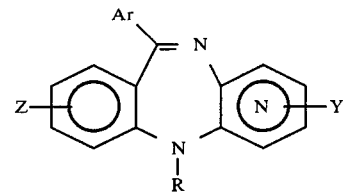

wherein;

R is selected from the group consisting of alkali-metal cation (M+), hydrogen, —alk$^1$—Q wherein Q is selected from hydrogen, halo, —NR$^1$R$^2$, —N=CH—OC$_2$H$_5$ or

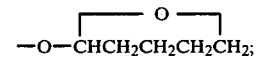

R$^1$ and R$^2$ are selected from the group consisting of loweralkyl, —C(O)—O—loweralkyl or R$^1$ and R$^2$ taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl;

Ar is selected from the group consisting of 2, 3 and 4-pyridinyl, 2 or 3-thienyl, phenyl or phenyl substituted by 1 to 3 adicals selected from halo, loweralkyl, loweralkoxy, trifluoromethyl or nitro and may be the same or different;

alk$^1$ is a straight or branched hydrocarbon chain containing 1-8 carbon atoms;

Z is selected from the group consisting of hydrogen, halogen, loweralkyl, loweralkoxy, hydroxy or nitro;

Y is selected from the group consisting of hydrogen or 1-2 radicals selected from loweralkyl, loweralkoxy or hydroxy and may be the same or different, and the acid addition salts thereof except when R=M+, which comprises the steps of:

Step 1, reacting a compound of the formula

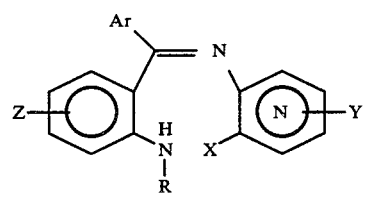

or a mixture of compounds of the formulas

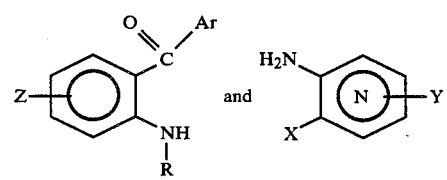

wherein Ar, Y and Z are as defined above and X is selected from chlorine, bromine, fluorine or iodine;

R is hydrogen or alk$^1$—Q wherein alk$^1$ is as defined above and Q is hydrogen, —NR$^1$R$^2$, —N=CH—OC$_2$H$_5$ or

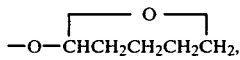

and

R[1] and R[2] are selected from loweralkyl, —C(O)O—loweralkyl, or R[1] and R[2] taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl, with at least a stoichiometric amount of a strong non-nucleophilic alkali-metal base in stirrable admixture with inert liquid carrier to give a compound of the formula

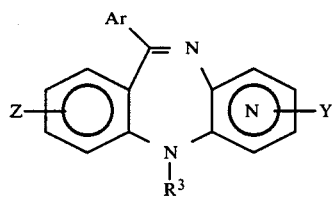

in said carrier, wherein Ar, Y and Z are as defined above, and R[3] is an alkali-metal ion consisting of sodium, potassium or lithium, or —alk[1]—Q wherein alk[1] is as defined above and Q is the same as in the starting compound;

Step 2, reacting a compound as prepared in said carrier in step 1 wherein R[3] is an alkali-metal ion with a proton source to give a compound of the formula:

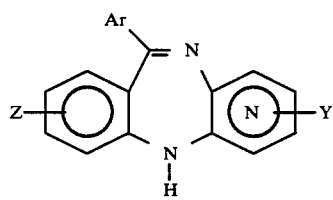

in said carrier, wherein Ar, Z and Y are as defined above.

Step 3, reacting a compound as prepared in said carrier in step 1 wherein R[3] is an alkali-metal ion with a reagent having the formula:

halo—alk[1]—Q wherein Q is selected from hydrogen, —NR[1]R[2], —N=CH—O—C$_2$H$_5$ or

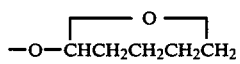

and R[1] and R[2] are as selected from the group consisting of loweralkyl, —C(O)—O—loweralkyl or R[1] and R[2] taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl, to give a compound of the formula:

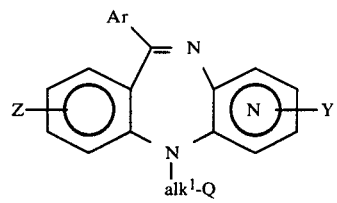

in said carrier, wherein Q has the starting value of said reagent and Ar, Y, Z and alk[1] are as defined above;

Step 4, separating a compound prepared in step 1, other than a compound wherein R[3] is an alkali-metal cation or a compound prepared in steps 2 or 3 by conventional means from said carrier and the reaction mixture to give a compound of the formula:

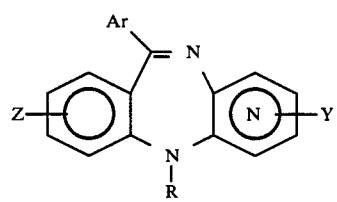

wherein Ar, Y, Z and R are as defined above, except R is not alkali-metal ion, and the acid addition salts thereof.

2. The process of claim 1 wherein in step 1, compounds of said formulas

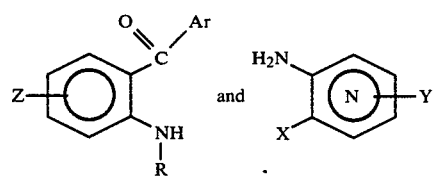

are reacted with said strong base.

3. The process of claim 1 wherein in step 1, compounds of said formulas

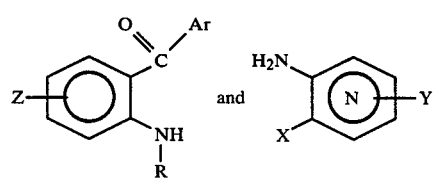

are reacted with said strong base consisting of sodium hydride.

4. The process of claim 1 wherein in step 1 a mixture of compounds of said formulas

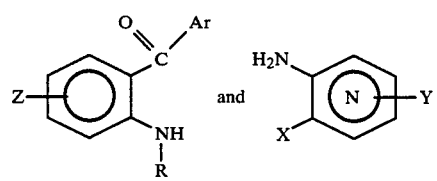

wherein R is H are reacted with said strong base.

5. The process of claim 1 wherein in step 1 a mixture of compounds of said formulas

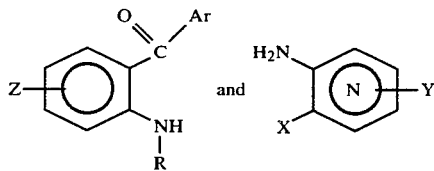

wherein R is H are reacted with strong base consisting of sodium hydride.

6. The process of claim 1 wherein in step 1 a mixture of compounds of said formulas

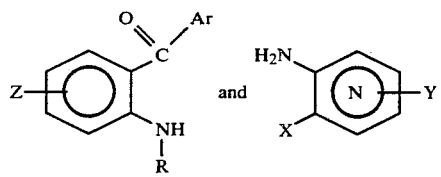

consisting of
2-aminobenzophenone, and
3-amino-2-chloropyridine
are reacted with sodium hydride to give in step 1 the sodium salt of 6-phenyl-11H-pyrido[2,3-b][1,4]benzodiazepine.

7. The process of claim 1 wherein in step 1 a mixture of compounds of said formulas

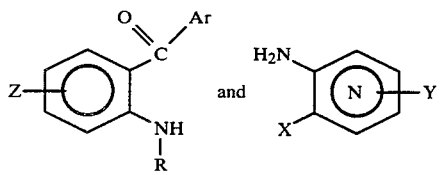

consisting of
[2-[[3-(dimethylamino)propyl]amino]phenyl]phenylmethanone, and
3-amino-2-chloropyridine
are reacted with sodium hydride in step 1 to give N,N-dimethyl-6-phenyl-11H-pyrido[2,3-b][1,4]benzodiazepine-11-propanamine.

8. The process of claim 1 wherein in step 1, a compound of said formula

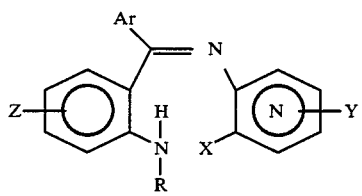

is reacted with said strong base.

9. The process of claim 1 wherein in step 1, a compound of said formula

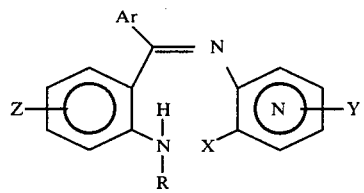

is reacted with said strong base consisting of sodium hydride.

10. The process of claim 1 wherein in step 1, a compound of said formula

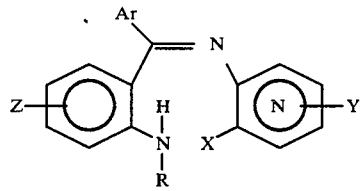

consisting of
N-[(2-aminophenyl)phenylmethylene]-2-chloro-3-pyridinamine
is reacted with said strong base.

11. The process of claim 1 wherein a tetrahydrofuran solution of a compound of said formula

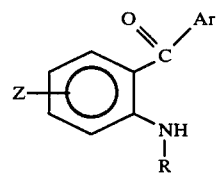

and a slurry of sodium hydride in toluene are added simultaneously to a boiling toluene solution of pyridine compound of said formula

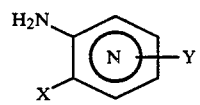

at a rate such that tetrahydrofuran or dioxane is distilled off at about the same rate it is being added and thereafter adding a toluene solution containing a reagent having said formula halo—alk¹—Q to give a compound having said formula

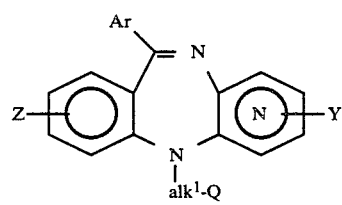

12. The process of claim 1 wherein in a preliminary step A, a compound of said formula

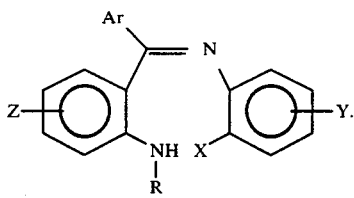

in said liquid carrier is prepared by reacting a mixture of a compound of said formula

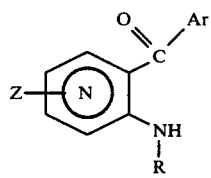

and a compound of said formula

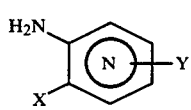

together with titanium tetrachloride and an excess of a tertiary organic amine in an inert liquid carrier and substantially separating the product from the reaction mixture by conventional means and using the product in said step 1.

13. A process for the preparation of a pyridobenzodiazepine compound having the formula:

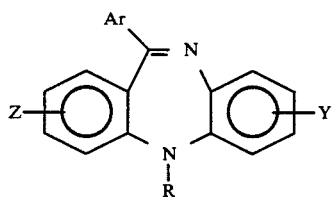

wherein;
R is selected from the group consisting of an alkali-metal cation, hydrogen, —alk$^1$—Q wherein Q is selected from hydrogen, halo, —NR$^1$R$^2$, —N═CH—OC$_2$H$_5$,

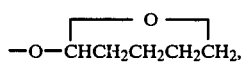

hydroxy or —OSO$_2$W wherein W is loweralkyl, phenyl or tolyl;
R$^1$ and R$^2$ are selected from the group consisting of hydrogen, loweralkyl, —C(O)—O—loweralkyl or R$^1$ and R$^2$ taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl;
Ar is selected from the group consisting of 2, 3 and 4-pyridinyl, 2 or 3-thienyl, phenyl or phenyl substituted by 1 to 3 radicals selected from halo, loweralkyl, loweralkoxy, trifluoromethyl or nitro and may be the same or different;
alk$^1$ is a straight or branched hydrocarbon chain containing 1-8 carbon atoms;
Z is selected from the group consisting of hydrogen, halogen, loweralkyl, loweralkoxy, hydroxy or nitro;
Y is selected from the group consisting of hydrogen or 1-2 radicals selected from loweralkyl, loweralkoxy or hydroxy and may be the same or different, comprising the steps of
Step A, reacting a mixture of a compound of the formula

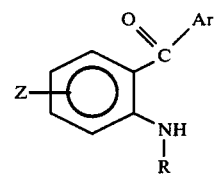

wherein Ar, Z and R are as defined above in this claim, except R is never alkali-metal ion and Q is never halo, hydroxy or —OSO$_2$W, and R$^1$ and R$^2$ are not hydrogen, and a compound of the formula

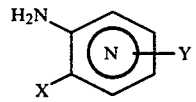

wherein X is halogen selected from chlorine, bromine, fluorine and iodine, and Y is as defined above in this claim together with titanium tetrachloride and an excess of a tertiary amine and an inert liquid carrier to give a compound of the formula

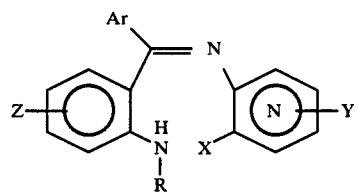

wherein Ar, Y, Z, X and R have the values given above in this claim and substantially separating it from the reaction mixture.
Step 1, reacting a compound prepared in step A or a mixture of compounds of the formulas

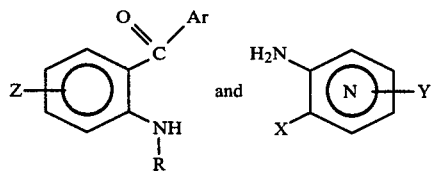

wherein Ar, Y, X, Z and R have the values as defined in step 1 with at least a stoichiometric amount of a strong non-nucleophilic alkali-metal base in stirrable admixture with inert liquid carrier to give a compound of the formula

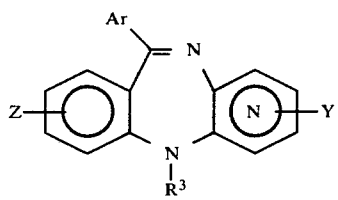

in said carrier of step 1 wherein;
Ar, Y and Z are as defined above in this claim, and $R^3$ is an alkali-metal ion consisting of sodium, potassium or lithium or $alk^1$—Q as defined in step A;

Step 2, optionally when desired, reacting a compound as prepared in said carrier in step 1 wherein $R^3$ is an alkali-metal ion with a proton source to give a compound of the formula

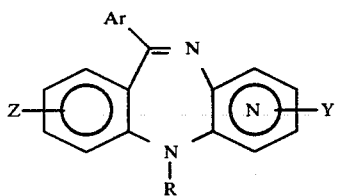

in admixture with said liquid carrier of step 1 wherein Ar, Z and Y are as defined above;

Step 3, when desired, reacting a compound as prepared in said carrier in step 1 wherein $R^3$ is an alkali-metal ion with a reagent having the formula

wherein Q is selected from hydrogen, $-NR^1R^2$, $-N=CH-OC_2H_5$ or $$-O-\overset{\lceil\quad\quad O\quad\quad\rceil}{CHCH_2CH_2CH_2CH_2}$$

and $R^1$ and $R^2$ are selected from the group consisting of loweralkyl, —C(O)—O—loweralkyl or $R^1$ and $R^2$ taken together with the adjacent nitrogen atom may form a heterocyclic residue selected from the group consisting of 1-piperidinyl, 1-phthalimido, 1-pyrrolidinyl, 4-morpholinyl, 1-piperazinyl and 4-substituted-piperazin-1-yl to give a compound of the formula

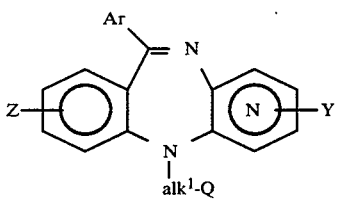

in said carrier wherein Q has the starting value of said reagent and Ar, Y, Z and $alk^1$ are as defined above;

Step 4, separating a compound prepared in step 1 other than a compound wherein $R^3$ is a alkali-metal cation or a compound prepared in steps 2 or 3 by conventional means from said carrier and the reaction mixture to give a compound of the formula

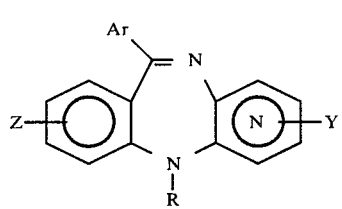

wherein Ar, Y, Z and R are as defined above, except R is not alkali-metal ion,
and the acid addition salts thereof;

Step 5, when desired, reacting a compound obtained in step 4 of the formula

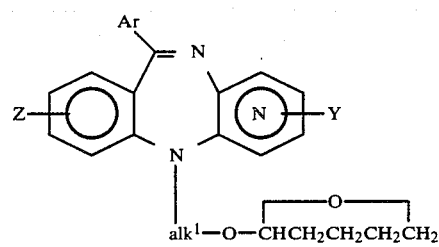

wherein Ar, Y, Z and $alk^1$ are as defined above with a strong concentrated acid in protic solvent, preferably ethanol, to give a compound of the formula

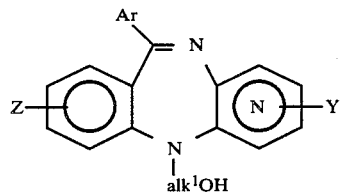

wherein Ar, Y, Z and $alk^1$ are as defined above;

Step 6, reacting a compound prepared in step 5 with thionyl chloride to obtain a compound of the formula

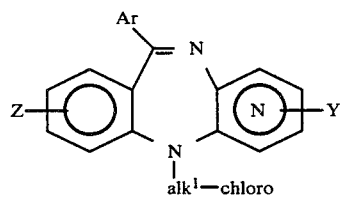

wherein Ar, Y, Z and $alk^1$ are as defined above;

Step 7, when desired, reacting a compound prepared in step 5 with a reagent of the formula $WSO_2Cl$ wherein W is loweralkyl, phenyl or tolyl to give a compound of the formula

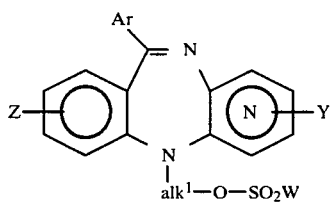

wherein Ar, Y, Z, alk¹ and W are as defined above;
Step 8, when desired, reacting a compound prepared in steps 6 or 7 with ammonia or a secondary or primary amine of the formula

HNR¹R² wherein $R^1$ and $R^2$ are as selected from hydrogen, loweralkyl, and —NR¹R² may be a heterocyclic radical to give a compound of the formula

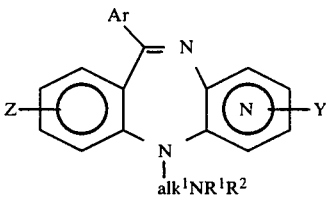

wherein Ar, Y, Z, alk¹ and $R^1$, $R^2$ and NR¹R² are as defined above.

* * * * *